United States Patent
Ichikawa et al.

(10) Patent No.: US 9,596,985 B2
(45) Date of Patent: Mar. 21, 2017

(54) COLOR-VIEWING FUNCTION MEASURING MEANS AND COLOR-VIEWING FUNCTION MEASUREMENT SYSTEM

(71) Applicants: SHINSHU UNIVERSITY, Nagano (JP); KOWA COMPANY, LTD., Aichi (JP); Kazuo Ichikawa, Aichi (JP)

(72) Inventors: Kazuo Ichikawa, Aichi (JP); Kiyoshi Tanaka, Nagano (JP); Tanaka Yoshiki, Nagano (JP)

(73) Assignees: Kazuo Ichikawa, Aichi (JP); Shinshu University, Nagano (JP); Kowa Company, Ltd, Aichi (JP)

( * ) Notice: Subject to any disclaimer, the term of this patent is extended or adjusted under 35 U.S.C. 154(b) by 0 days.

(21) Appl. No.: 14/395,641

(22) PCT Filed: Apr. 17, 2013

(86) PCT No.: PCT/JP2013/061386
§ 371 (c)(1),
(2) Date: Oct. 20, 2014

(87) PCT Pub. No.: WO2013/157573
PCT Pub. Date: Oct. 24, 2013

(65) Prior Publication Data
US 2015/0085258 A1    Mar. 26, 2015

(30) Foreign Application Priority Data
Apr. 18, 2012    (JP) .................................. 2012-094639

(51) Int. Cl.
*A61B 3/02*    (2006.01)
*A61B 3/06*    (2006.01)
(Continued)

(52) U.S. Cl.
CPC ............ *A61B 3/066* (2013.01); *A61B 3/0041* (2013.01); *A61B 3/032* (2013.01)

(58) Field of Classification Search
CPC ....... A61B 3/0033; A61B 3/0041; A61B 3/06; A61B 3/063; A61B 3/066
(Continued)

(56) References Cited

U.S. PATENT DOCUMENTS 2,937,567 A * 5/1960 Ferree .................... A61B 3/066
351/242
4,615,594 A * 10/1986 Task ....................... A61B 3/063
351/239
(Continued)

FOREIGN PATENT DOCUMENTS

JP        209849       7/2002
JP        241808       9/2005
(Continued)

*Primary Examiner* — Huy K Mai
(74) *Attorney, Agent, or Firm* — Law Offices of Robert F. Zielinski, LLC (57) ABSTRACT

[Problem] To be able to accurately measure color vision and color-viewing field for different colors.
[Solution] The color-viewing function measuring means (1) pertaining to the present invention displays a plurality of chromatically colored targets ($A_{11}$, . . . ) (for example, Landolt rings) in an achromatic background (B), the brightness of the targets ($A_{11}$, . . . ) being set so as to be substantially equal to the brightness of the background (B). When vision or the viewing field is measured with this color-viewing function measuring means (1), vision and viewing field can be accurately measured for different colors.

9 Claims, 8 Drawing Sheets

(51) Int. Cl.
*A61B 3/032* (2006.01)
*A61B 3/00* (2006.01)

(58) Field of Classification Search
USPC .................................... 351/242, 239
See application file for complete search history.

(56) References Cited

U.S. PATENT DOCUMENTS

| | | | |
|---|---|---|---|
| 5,461,436 A | 10/1995 | Campbell | |
| 6,379,007 B1* | 4/2002 | Farb | A61B 3/028 351/239 |
| 2004/0207813 A1 | 10/2004 | Suzuki | |
| 2006/0209258 A1* | 9/2006 | Nareppa | A61B 3/066 351/242 |

FOREIGN PATENT DOCUMENTS

| | | |
|---|---|---|
| JP | 005573 | 1/2012 |
| JP | 11146 | 1/2012 |
| JP | 145080 | 7/2013 |
| WO | WO 2010032592 A1 | 3/2010 |

* cited by examiner

F I G. 8

COLOR-VIEWING FUNCTION MEASURING MEANS AND COLOR-VIEWING FUNCTION MEASUREMENT SYSTEM

TECHNICAL FIELD

This invention relates to color-viewing function measuring means and a color-viewing function measurement system for measuring color vision and/or a color-viewing field of an examinee.

BACKGROUND ART

It was common to use white or black targets in order to measure a vision or a field of view in the past (for example, patent related document 1 shown below). But, we are surrounded by many chromatically colored materials, and in fact, there are few white or black materials in our circumstances. Then, recently, measurement of vision or field of view adding influences of colors is increasingly attracting attention, but not measurement with white or black targets. And, various methods are proposed (for example, see patent related documents 2 and 3 shown below).

PRIOR ART

Patent Related Document

[Patent related document 1]: Japanese patent application publication No. 2012-11146
[Patent related document 2]: Japanese patent application publication No. 2002-209849
[Patent related document 3]: Specification of The U.S. Pat. No. 5,461,436

SUMMARY OF INVENTION

Problems to be Solved by Invention

Figure 3:
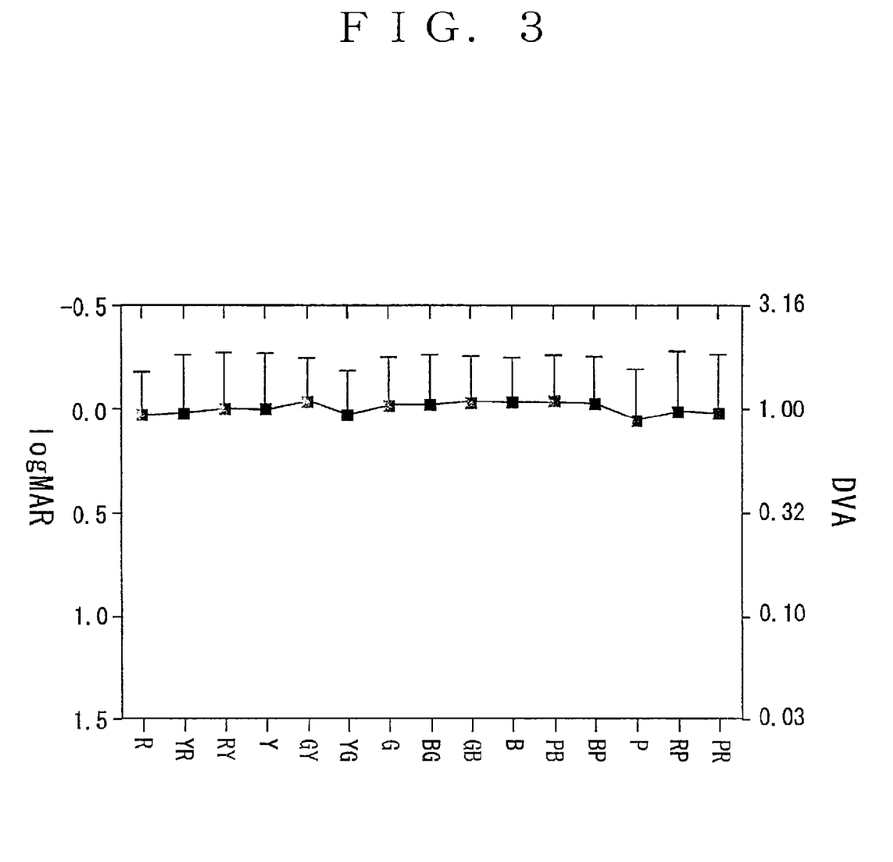
FIG. 3 is a view that shows measurement results when measuring a color vision with a conventional method.

Inventors of the invention have measured vision of respective colors with an inspection table where fifteen (15) colored Landolt rings are shown in a gray background. In this case, brightness of the background is 100 [cd/m$^2$], brightness of the targets is 30 [cd/m$^2$] and the colors of targets are R, YR, RY, Y, GY, YG, G, BG, GB, B, PB, BP, P, RP, PR (fifteen colors of NEW COLOR TEST). FIG. 3 shows the measurement results, and colors are indicated in a lateral axis and visions are indicated in a longitudinal axis. It is clearly shown in FIG. 3 that the vision was constant in spite of the colors of the targets. That is, this results means only color taste of each target does not influence the measurement results although the targets used for the measurement are colored, that is, such results are almost the same as the measurements of vision with white or black targets although vision was measured with colored targets, and it was not possible to accurately measure color vision (that is, the vision receiving the influences of color taste and saturation).

As know from the above, the means for correctly measuring the color vision or the color-viewing field every each color did not exist in the past.

An object of the invention is to provide color-viewing function measuring means and a color-viewing function measurement system with which the above-mentioned problems can be solved.

Means for Solving Problems

Figure 1:
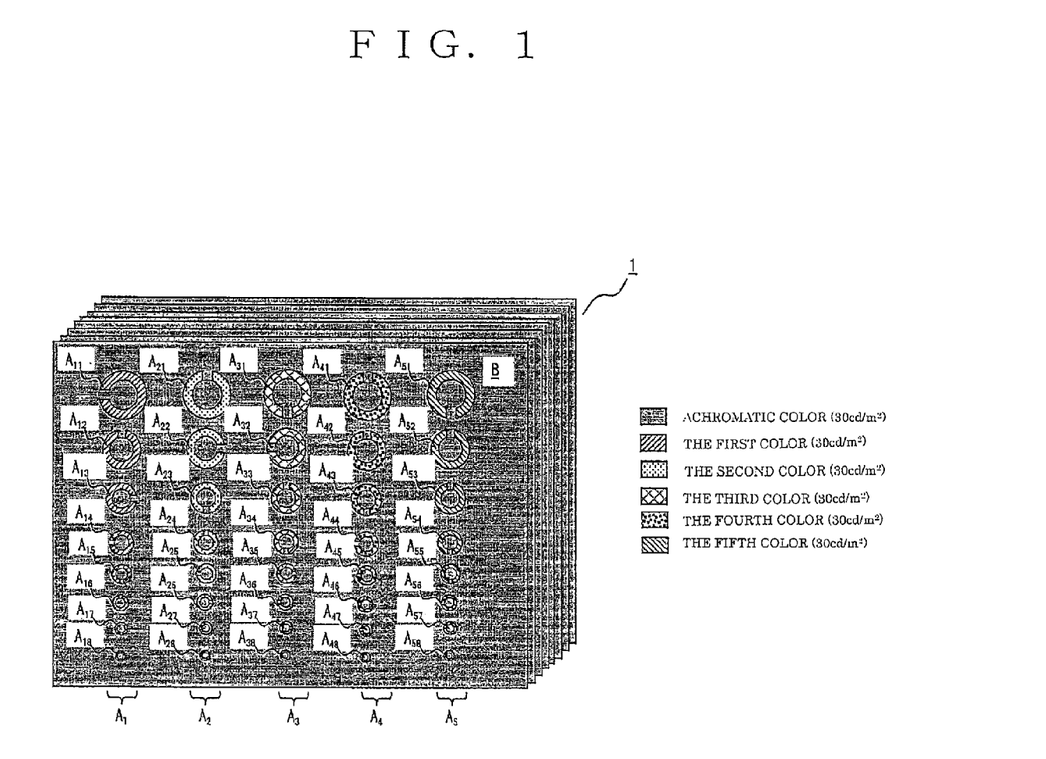
FIG. 1 is a schematic view that shows an example of a structure of color-viewing function measuring means according to the invention.
Figure 2:
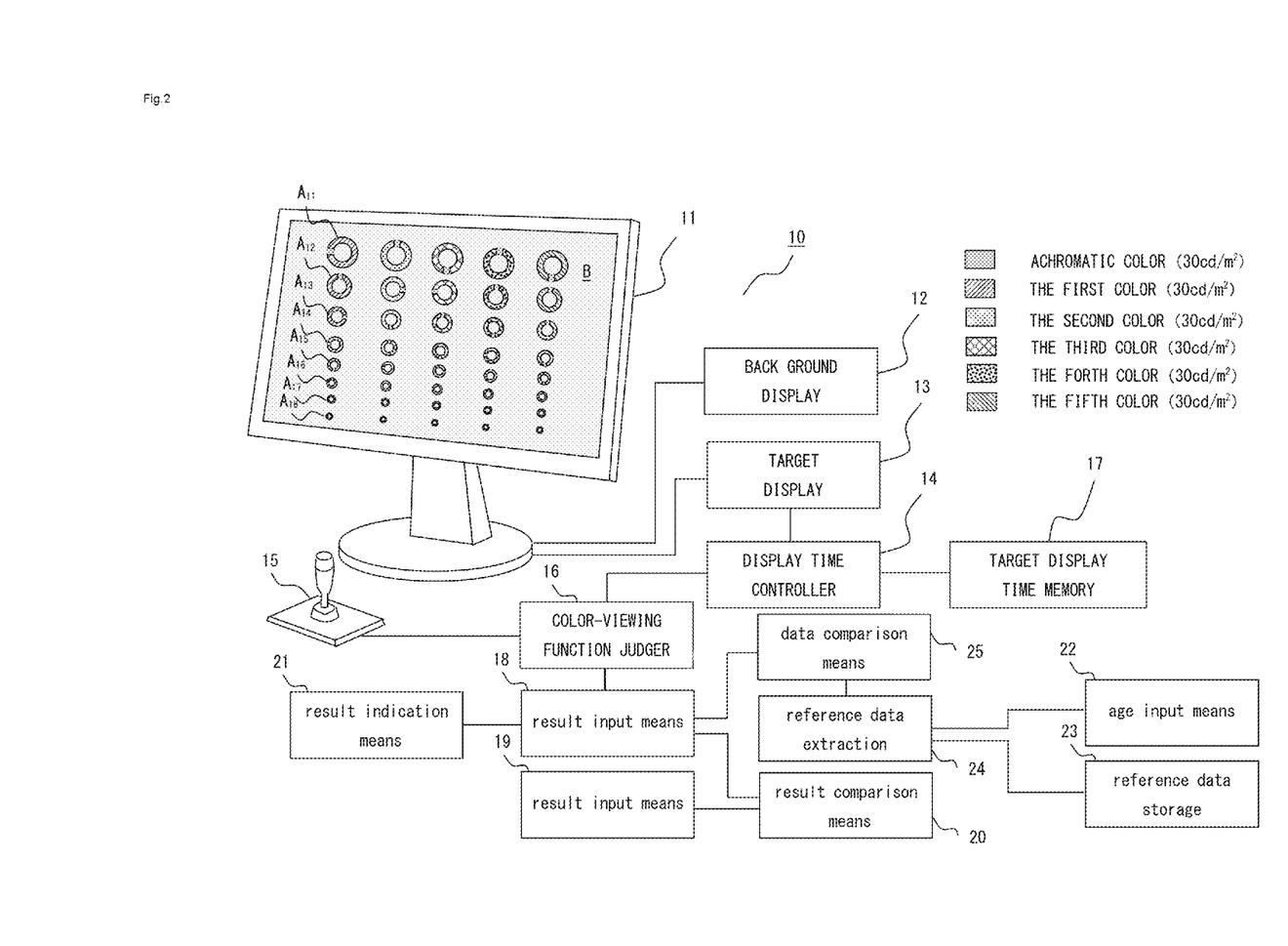
FIG. 2 is a schematic view that shows another example of the structure of the color-viewing function measuring means according to the invention.

The invention according to claim 1 is exemplified in FIGS. 1 and 2, and is color-viewing function measuring means (1, 10) that indicates a plurality of targets ($A_{11}$ ...) that are colored in chromatic colors on a background (B) and is possible to measure color vision and/or a color-viewing field that is a color-viewing function of an examinee by testing whether the examinee can perceive each target ($A_{11}$ ...), comprising:

all of the plurality of targets ($A_{11}$ ...) or at least a predetermined number of the plurality of targets ($A_{11}$ ...) being colored in almost the same chromatic color; and brightness of the targets ($A_{11}$ ...) being set so as to almost equal to brightness of the background (B);

whereby it is possible to measure a color vision and/or a color-viewing field regarding the chromatic color.

The invention according to claim 2 is the color-viewing function measuring means according to claim 1, wherein the brightness of all of the plurality of targets ($A_{11}$ ...) or the brightness of the predetermined number of targets ($A_{11}$ ...) are set almost equal to each other, and the following formula holds if the brightness of the target is α [cd/m2] and the brightness of the background is β [cd/m2]

$$-10 \leq \alpha - \beta \leq +10 \qquad \text{[Formula 1]}.$$

The invention according to claim 3 is color-viewing function measuring means according to claim 1 or 2, wherein the background (B) is an achromatic color.

The invention according to claim 4 is color-viewing function measuring means according to one of claims 1 to 3, wherein all of the plurality of targets ($A_{11}$ ...) or the predetermined number of targets ($A_{11}$ ...) are set to be different in their sizes, and it is possible to measure the color vision regarding the chromatic color of the examinee by testing whether the examinee can perceive each target ($A_{11}$ ...).

The invention according to claim 5 is color-viewing function measuring means according to one of claims 1 to 3, wherein all of the plurality of targets ($A_{11}$ ...) or the predetermined number of targets a ($A_{11}$ ...) are set to be almost equal to each other in their sizes, and it is possible to measure the color-viewing field regarding the chromatic color of the examinee by testing whether the examinee can perceive respective targets ($A_{11}$ ...) presented at various positions.

The invention according to claim 6 is exemplified in FIG. 1, and is color-viewing function measuring means according to one of claims 1 to 5, wherein the color-viewing function measuring means is a paper or a resin sheet on which the background (B) and the targets ($A_{11}$ ...) are indicated.

The invention according to claim 7 is exemplified in FIG. 2, and is color-viewing function measuring means according to one of claims 1 to 5, wherein a display (11) that is comprised of at least one of a liquid crystal display, a plasma display, an organic EL display and a CRT, a background indicator (12) that indicates the background (B) on the display (11), and a target indicator (13) that indicates the targets ($A_{11}$ ...) having a predetermined brightness, a predetermined color and a predetermined size on the display (11).

The invention according to claim 8 is exemplified in FIG. 2, and color-viewing function measuring means according to claim 7, wherein an indication time controller (14) that restricts time to indicate the target ($A_{11}$ ...) through the target indicator (13), a perception detector (15) that outputs signal indicating that the examinee perceived the indicated target ($A_{11}$ ...), and a color-viewing function judger (16) that judges the color vision and/or the color-viewing field based upon the signals from the perception detector (15).

The invention according to claim 9 is color-viewing function measuring means according to claim 7, wherein a target indication time memory (17) that stores target indication time every each color, an indication time controller (14) that restricts the time to indicate the target ($A_{11}$ . . . ) through the target indicator (13) to the target indication time every each color that is stored in the target indication time memory (17), and a perception detector (15) that outputs signals indicating that the examinee perceived the indicated target ($A_{11}$ . . . ), and a color-viewing function judger (16) that judges the color vision and/or the color-viewing field of the examinee based upon the signals from the perception detector (15).

The invention according to claim 10 is color-viewing function measurement system, comprising:

result input means that inputs measurement results regarding a color-viewing function that was measured through the color-viewing function measuring means according to one of claims 1 to 9;

result input means that inputs measurement results regarding normal vision function that does not receive influences of color taste; and result comparison means that compare the measurement results regarding the color-viewing function and the measurement results regarding normal vision function with each other or indicates both.

The invention according claim 11 is color-viewing function measurement system, comprising:

result input means that inputs measurement results regarding the color-viewing function that was measured through the color-viewing function measuring means according to one of claims 1 to 9; and result indication means that three-dimensionally indicates the measurement results inputted through the result input means on a chromaticity diagram The invention according to claim 12 is color-viewing function measurement system, comprising:

result input means that inputs measurement results regarding the color-viewing function that was measured through the color-viewing function measuring means according to one of claims 1 to 9;

age input means that inputs age of the examinee that was measured through the color-viewing function measuring means;

a reference data storage that stores reference data regarding the color-viewing function every each age;

a reference data extraction that extracts the reference data corresponding to age data from the reference data storage based upon the age data inputted through the age input means; and data comparison means that compares the measurement results inputted through the result input means and the reference data extracted through the reference data extraction with each other.

The number in parentheses shows the corresponding element in the drawings for the sake of convenience, accordingly, the descriptions are not restricted and bound by the descriptions on the drawings.

Effects of Invention

According to the invention of claims 1 through 7, it is possible to correctly measure the color vision and the color-viewing field.

According to the invention of claim 8, it is possible to easily judge the color-viewing function of the examinee (the color vision, the color-viewing field and the degree of fatigue).

According to the invention of claim 9, it is possible to set the target indication time in proper time every each color and to shorten the time required for the whole measurement so as to improve the efficiency of the measurement works.

According to the invention of claim 10, it is possible to easily compare the color vision of the examinee and the normal vision (that is, the vision that does not receive the influences of the color taste) with each other.

According to the invention of claim 11, it is possible to visually grasp superiority or inferiority of the color vision function for each color.

According to the invention of claim 12, it is possible to compare the color-viewing function of the examinee (the measurement results) and the reference data for each age with each other.

BRIEF DESCRIPTION OF DRAWINGS

FIG. 4(*a*) is a xy chromaticity diagramaled FIG. 4(*b*) is a Lab chromaticity diagram.

FIG. 6(*a*) to (*e*) are views that show measurement results when measuring the color vision for five examinees.

FIG. 7(*a*) is a view that shows measurement results of the color vision of examinees in the second decade and the sixth decade, and FIG. (b) is a chart indicating averaged measurement values in the second decade and the sixth decade and differences between both values every each color.

EMBODIMENTS FOR CARRYING OUT THE INVENTION

Embodiments of the invention are now mentioned, referring to appended drawings FIGS. 1 to 8.

In this specification, vision every each color, such as an ability to recognize red objects or blue objects with eyes, is referred to as "color vision", and a field of view every each color, such as a range of a perimetric view that can perceive red or blue without moving eyes is referred to as "color-viewing field", and the color vision and the color-viewing field are collectively referred to as "color-viewing function".

Color-viewing function measuring means according to the invention is for measuring the color vision and/or the color-viewing field of an examinee. The color-viewing function is exemplified as reference numbers 1 and 10 in FIG. 1 and FIG. 2, and indicates a plurality of targets, such as $A_{11}$ (that is, Landolt rings mentioned hereinafter or the other well-known targets) on a background B, and all of a plurality of targets $A_{11}$ . . . or at least a predetermined number of targets $A_{11}$ . . . are colored in almost the same chromatic color (that is, the chromatic color having almost equal color taste). In the color-viewing function measuring means 1, 10 as shown in FIGS. 1 and 2, all targets indicated are colored in respectively different five colors, such as the first color through the fifth color, but such a coloration is not restrictive, needless to say. All targets indicated may be respectively colored in one color, such as red, different two to four colors, or six or more colors. Besides, number of the targets indicated on the color-viewing function measuring means 1, 10 as shown in FIGS. 1 and 2 is forty (40), but such a number is not restrictive, and the number of the targets can be optionally set. Furthermore, the targets in achromatic color (that is, saturation is zero) may be indicated in addition to ones in chromatic color. And, the color-viewing function measuring means 1 and 10 as shown in FIGS. 1 and 2 simultaneously indicate all targets $A_{11}$ . . . , but such an indication is not restrictive, and one or several targets may be indicated in order.

In this case, brightness (lightness) of at least predetermined number of targets $A_{11}$ of a plurality of targets $A_{11}$ . . . and brightness (lightness) of background B are almost equal to each other, and it is possible to measure the color vision and/or the color-viewing field regarding the chromatic colors by testing whether the examinee can perceive such target $A_{11}$ . . . The targets and the background are set to be different in at least one of hue and saturation (or in both). Preferably, the brightness of the background B is set as 20 to 100 [$cd/m^2$] (for instance, 30 [$cd/m^2$]), and when the brightness of the targets $A_{11}$ . . . is $\alpha$ [$cd/m^2$] and the brightness of the background B is $\beta$ [$cd/m^2$], the following formula holds. That is, $$-10 \le \alpha - \beta \le +10 \quad \text{[Formula 2]}$$

In such a case, the color of the background B may be a chromatic color (that is, the color which saturation is not zero) or an almost achromatic color (that is, the achromatic color which saturation is zero or the achromatic color into which slightly chromatic color is mixed). For instance, the background may be gray and the targets may be some chromatic color as mentioned hereinafter.

Besides, the background B may be a specific chromatic color and the targets $A_{11}$ . . . may be a chromatic color (for instance, the background B may be red and the targets $A_{11}$ . . . may be red which saturation is different from the background B, or the background B may be green and the targets $A_{11}$ . . . may be red). Preferably, the background in almost achromatic color is used for the examination of eye disease. Preferably, the background in chromatic color is used for the examination of degree of fatigue of normal eyes.

Preferably, it is possible to measure the color vision regarding the chromatic color of the examinee in such a way that all of a plurality of targets $A_{11}$ . . . or a predetermined number of targets $A_{11}$ . . . (that is, a plurality of targets that are colored in chromatic color having almost equal color taste) are set to be gradually different in their sizes so as to test whether or not the examinee can perceive each target $A_{11}$ . . . .

Otherwise, it may possible to measure the color-viewing field regarding the chromatic color of the examinee in such a way that all of a plurality of targets $A_{11}$ . . . or a predetermined number of targets $A_{11}$ . . . (that is, a plurality of targets that are colored in chromatic color having almost equal color taste) are set to be almost equal in their sizes so as to test whether or not the examinee can perceive the respective targets that are presented at various positions. When the color vision is measured through the above-mentioned color-viewing function measuring means 1, 10, the size of the colored target that the examinee can perceive is known, so that the colored target of that size is used for the examination of the color-viewing field, preferably. Besides, a plane perimeter may be used since it is sufficient to measure the visual field in a center part in case of the measurement of the color-viewing field.

Subsequently, effects of the invention are now mentioned.

Figure 4:
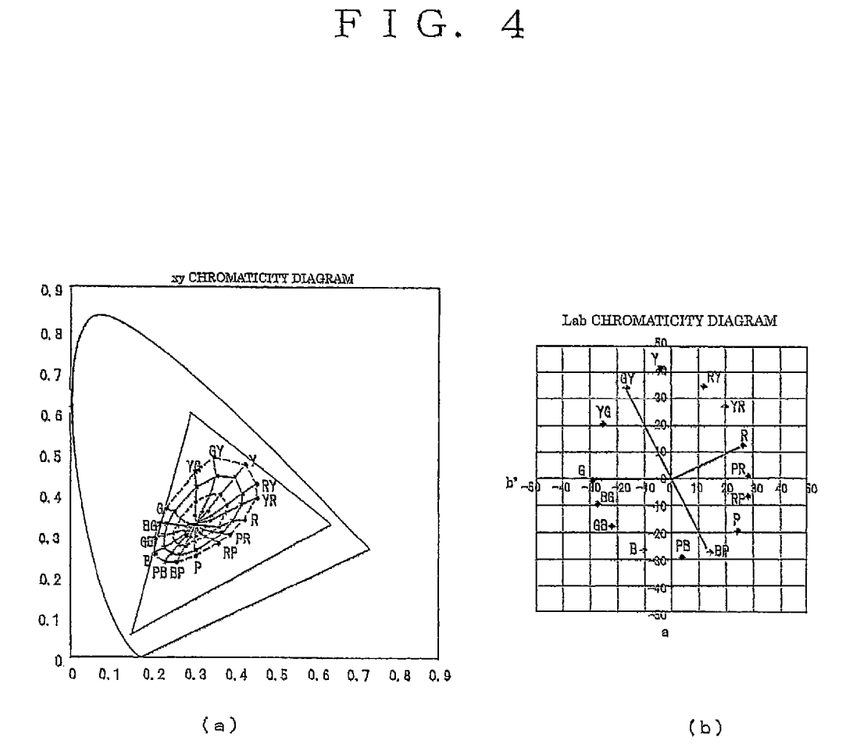

Such trials to measure the color vision with the targets colored in chromatic colors (colored targets) have been performed in a field of an examination of the vision. But, in such trials the difference of the brightness between the background and the target was not adjusted as this invention, and the measurement result (the color vision) is as shown in FIG. 3, for instance, and the measurement results are almost constant in spite of the color of the target. This result means that the color taste of each target does not affect the measurement results although the targets used for the measurement are colored (that is, the measurement result is almost the same as the measurement result that has been measured with the targets in white or black although the examination has been performed with the colored targets), and it was not possible to correctly measure the color vision). Fifteen colors of NEW COLOR TEST (R, YR, RY, Y, GY, YG, G, BG, GB, B, PB, BP, P, RP, PR) have been used as the colors of the targets (see FIGS. 4(a) and (b)), and the fifteen color's are indicated in a lateral axis and the visions are indicated in a longitudinal axis in FIG. 3. And, the background is grey, and the brightness of the background is 100 [$cd/m^2$], and the brightness of the targets is 30 [$cd/m^2$].

Figure 5:
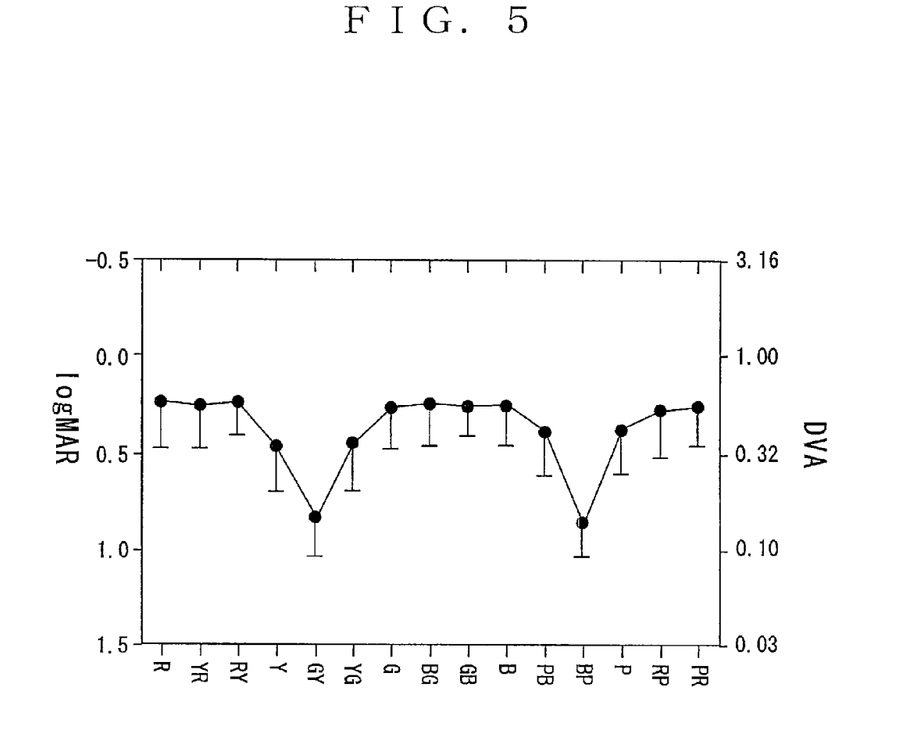
FIG. 5 is a view that shows measurement results when measuring a color vision with the color-viewing function measuring means according to the invention.

On the other hand, the measurement results of the vision through the color-viewing function measuring means 1, 10 according to the invention is as shown FIG. 5. In FIG. 5 fifteen colors of NEW COLOR TEST (R, YR, RY, Y, GY, YG, G, BG, GB, B, PB, BP, P, RP, PR) have been used as the colors of the targets (see FIGS. 4(a) and (b)), and the fifteen colors are indicated in a lateral axis and the visions are indicated in longitudinal axis. And, the background is grey, and the brightness of the background is 30 [$cd/m^2$], and the brightness of the targets is 30 [$cd/m^2$]. According to FIG. 5, the color vision of GY and BP drops, but this (that is, the drop of the color vision of GY and BP) is not important, but such a point that the measured color vision is not constant as FIG. 3, but is widely different, depending the colors is important. Such a fact that the measured color vision varies according to the colors means the color taste of the target affects the measurement result and it was possible to measure the vision every each color (that is, the color vision). Besides, when measuring the color-viewing field through the color-viewing function measuring means 1, 10 according to the invention, it is possible to measure the visual field every each color (the color-viewing field), and according to the invention, it is possible to correctly measure the color vision and the color-viewing field every each color. It is known that the vision of R color of elderly persons is inferior in comparison with their vision of the other colors, and it is known that the vision of a specific color of persons who suffer from eye diseases is inferior in comparison with their vision of the other colors. But, according to the invention, it is possible to correctly measure such a deterioration of the vision every each color. That is, a color has three elements, such as hue, lightness (brightness) and saturation. In the invention, the lightness of the background and the lightness of the targets are set to be almost equal to each other, so that the examiners recognize the targets by the difference of the hue or the difference of the saturation.

Preferably, the above-mentioned color-viewing function measuring means indicates the background in an almost achromatic color and the target in an almost achromatic color and different from the background in the brightness, the background in a chromatic color and the target in the chromatic color and almost the same as the background in the brightness, or the background in an almost achromatic color and the target in a chromatic color and almost the same as the background in the brightness.

As exemplified as the reference number 10 in FIG. 2, the color-viewing function measuring means is for example a device which is comprised of a display 11 that is comprised of at least one of a liquid crystal display, a plasma display, an organic EL display, a CRT and the other well-known displays, a background indicator 12 that indicates the background B on the display 11, and a target indicator 13 that indicates the targets $A_{11}$ . . . having a predetermined brightness, a predetermined color and a predetermined size on the display 11. According to the invention, it is not necessary to strictly synchronize the brightness of the background B and the brightness of the targets $A_{11}$ . . . , so that a device and a control for strictly synchronizing both brightness is not necessary and the device can be made cheaper. In such a case, a perception detector that outputs signals indicating that the examinee perceived the indicated target $A_{11}$ . . . , a perception time measurer that measures time from the presentation of the target $A_{11}$ . . . to the perception by the examinee based upon the signal from the perception detector, and a color-viewing function judger that judges the color vision and/or the color viewing field of the examinee from the size or the position of the presented target and the time that was measured through the perception time measurer may be provided. If provided, it is possible to judge the color vision or the color-viewing field, taking the time necessary for the perception into consideration in addition to whether the target can be perceived, and it is possible to correctly judge. Besides, an indication time controller 14 that restricts the time to indicate the target $A_{11}$ . . . through the target indicator 13 into a prescribed time, such as 0.5 second and 2.0 second, a perception detector 15 that outputs a signal indicating that the examinee perceived the indicated target $A_{11}$ . . . , and a color-viewing function judger 16 that judges the color vision and/or the color-viewing field of the examinee based upon the signals from the perception detector 15 may be provided. If provided, it is easily judge the color-viewing function of the examinee, such as the color vision, the color-viewing field the degree of fatigue (for example, with ○ or X). Since the time required for the perception of the target by normal eyes depends on the colors of the target, a target indication time memory 17 that stores the target indication time (prescribed time) every each color, the indication time controller 14 that restricts the time to indicate the target through the target indicator 13 to the target indication time every each color that is stored in the target indication time memory (17) (prescribed time), the perception detector 15 that outputs the signal indicating that the examinee perceived the indicated target and the color-viewing function judger 16 that judges the color vision and/or the color-viewing field of the examinee based upon the signals from the perception detector 15 may be provided. If such are provided, it is possible to properly set the target indication time every each color and shorten the whole time required for the measurement so as to improve efficiency of measurement works. Preferably, the target indication time is changed according to kinds of eye diseases. That is, the target indication time memory 17 for storing the target indication time every each color and every eye each disease (prescribed time), the indication time controller 14 that restricts the time to indicate the target through the target indicator 13 to the target indication time that is stored in the target indicator time memory 17 (prescribed time), the perception detector 15 that outputs the signal indicating that the examinee perceived the indicated target and the color-viewing function judger 16 that judges the color vision and/or the color-viewing field of the examinee based upon the signals from the perception detector 15 may be provided. Preferably, in a case of the target having the color which can be perceived by normal eyes in 0.2 second, such a target is presented to patients predetermine several times of 0.2 second (such as four times), and in a case of the target having the color which can be perceived by normal eyes in 0.5 second, such a target is presented to patients predetermine several times of 0.5 second (such as four times). If so, it is possible to properly set the target indication time for the patients every each color and every each eye disease and to shorten the time required for the whole measurements so as to improve the measurement works. The target indication time or the color of the target may be changed by the condition of the eye disease, such as an initial stage and a terminal stage. The above-mentioned perception detector 15 are for instance a joy stick and a button that are operated by the examinees or the examiners.

The color-viewing function measuring means are for example a paper, a resin sheet and a booklet, on which the background B and the targets $A_{11}$ . . . are indicated (printed) (see the reference number 1 of FIG. 1). According to the invention, it is not necessary to strictly synchronize the brightness of the background B and the brightness of the targets $A_{11}$ . . . and is sufficient to set both to be almost equal to each other. Then, it is possible to easily print these on the paper or the resin sheet with well-known methods. The colors in which vision deteriorates are different according to the kinds of the eye diseases. So, it is sufficient to prepare a vision test chart every each eye disease and to preferentially measure the vision of the person who suffers from the eye disease for necessary color only.

On the other hand, a color-viewing function measurement system may be comprised of result input means that inputs measurement results regarding the color-viewing function measured through the above-mentioned color-viewing function measuring means 1, 10, result input means that inputs measurement results regarding the normal vision function that does not receive the influence of color taste (that is, the vision or the field of view that does not receive the influence of color taste, that is measured with the targets in almost achromatic color, such as white and black, or the targets different from the back ground in the brightness more than the predetermined brightness phases), and result comparison means that compares the measurement results regarding the color-viewing function and the measurement results regarding the normal vision function with each other or indicates both. According to the color-viewing function measurement system, it is possible to easily compare the color vision of the examinee and the normal vision of the examinee (that is, the vision that does not receive the influences of the color taste) with each other.

Figure 8:
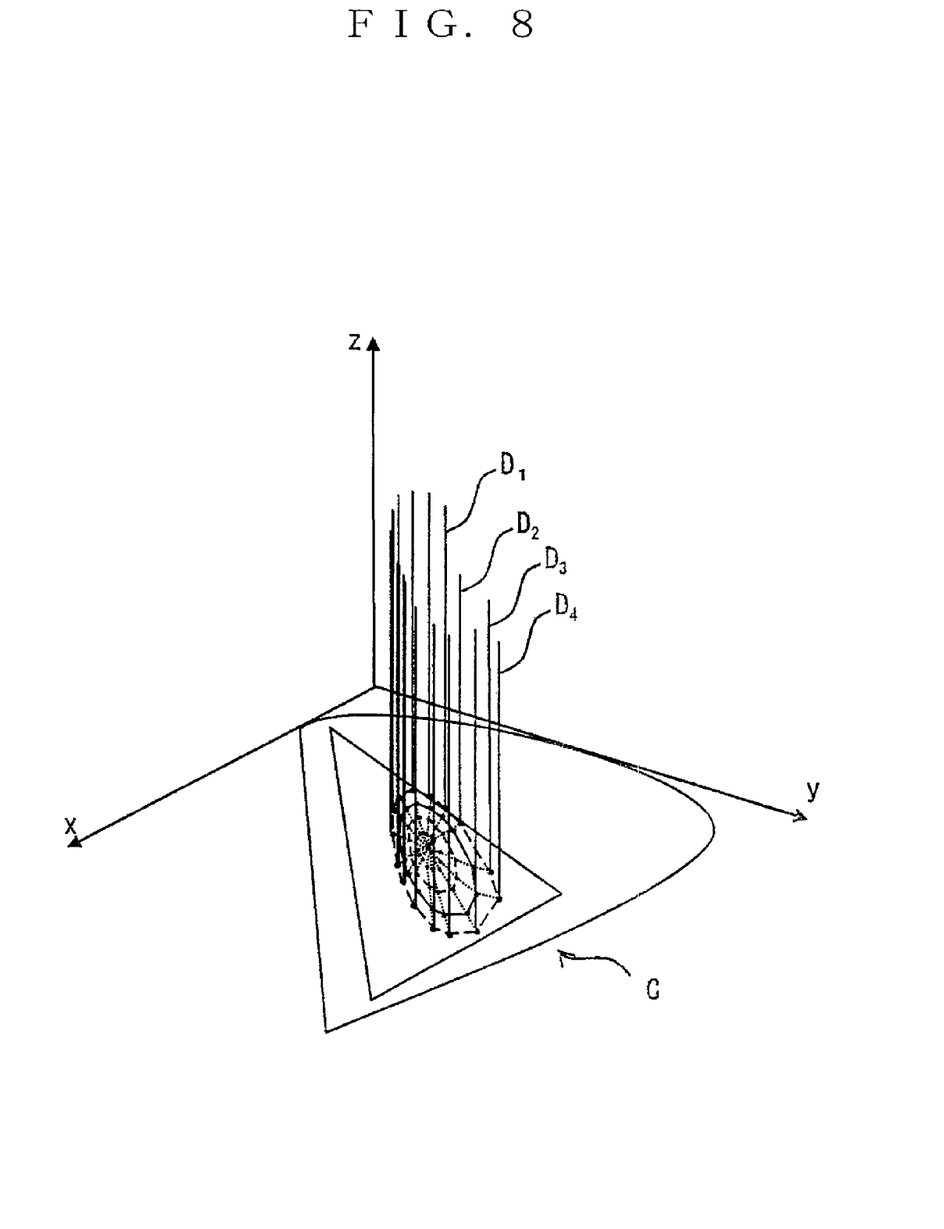
FIG. 8 is a view three-dimensionally indicating measurement results of the color vision.

Besides, the color-viewing function measurement system may be comprised of the result input means that inputs the measurement results regarding the color-viewing function that was measured through the color-viewing function measuring means 1, 10 and result indication means that three-dimensionally indicates the measurement results inputted through the result input means on a chromaticity diagram. FIG. 8 is an example of the figure indicated by the result indication means. A reference number C in the figure denotes the chromaticity diagramaled a reference number $D_1$ . . . denotes a line showing the color-viewing function of each color, such as the color vision. According to the color-viewing function measurement system, it is possible to visually grasp superiority or inferiority of the color-viewing function every each color.

Furthermore, the color-viewing function measurement system may be comprised of the result input means that inputs the measurement results regarding the color-viewing function that was measured through the color-viewing function measuring means 1, 10, age input means that inputs age of the examinee that was measured through the color-viewing function measuring means 1, 10, reference data storage that stores reference data regarding the color-viewing function for each age, a reference data extraction that extracts the reference data corresponding to the age data from the reference data storage based upon the age data inputted through the age input means, and data comparison means that compares the measurement results inputted through the result input means and the reference data extracted through the reference data extraction with each other. According to the color-viewing function measurement system, it is possible to compare the color-viewing function of the examinee (the measurement results) and the reference data for each age with each other.

Embodiment 1

Figure 6:
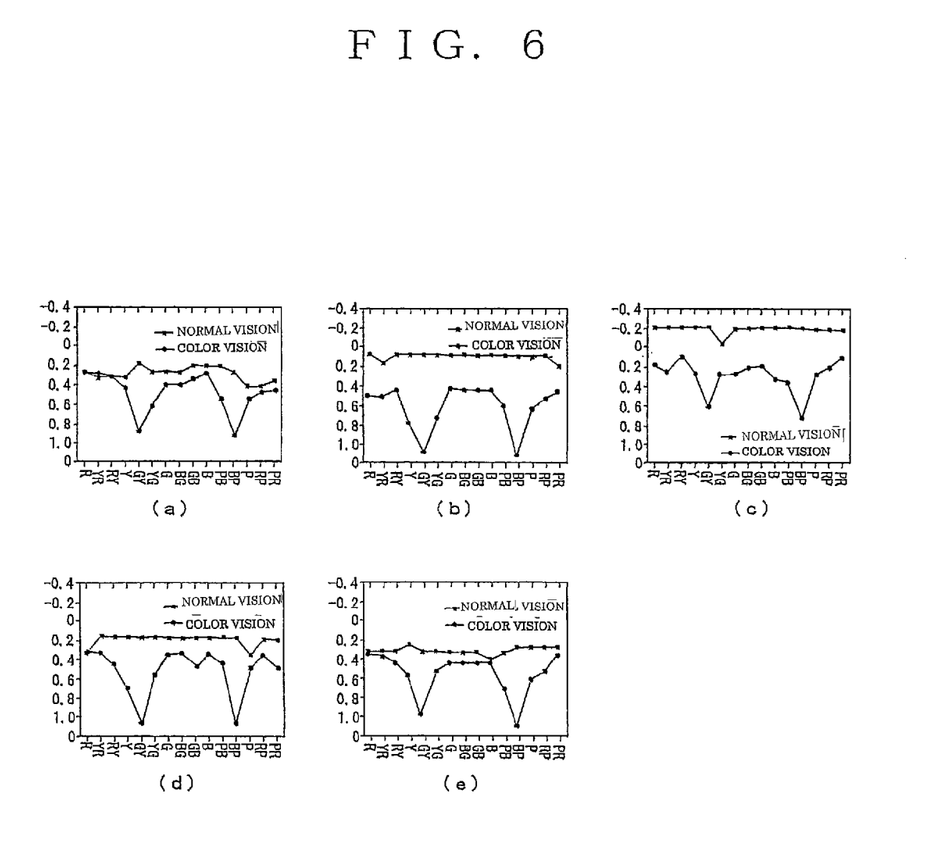

Embodiment 1 of the invention is now mentioned, referring to appended FIGS. 1 and 6.

In this embodiment, the color vision was measured with a vision test chart 1 as shown in FIG. 1 (color-viewing function measuring means). The vision test chart 1 as shown in FIG. 1 is possible to measure five colors of color visions since the Landolt rings (the targets) are colored in five colors. But, in this embodiment, the Landolt rings colored in fifteen colors of NEW COLOR TEST, such as R, YR, RY, Y, GY, YG, G, BG, GB, B, PB, BP, P, RP, PR have been used and the color vision for such fifteen colors have been measured. And, the color of the background was gray and the brightness of the each target $A_{11}$ . . . and the background B was 30 [cd/m$^2$].

FIGS. 6 (a) to (e) show the measurement results of five examinees, and colors of the respective targets are indicated in a lateral axis and visions are indicated in a longitudinal axis. A normal vision in the figure is the vision that was measured with the brightness of the background B 100 [cd/m$^2$] and the brightness of the target $A_{11}$ . . . 30 [cd/m$^2$]. The color vision is the vision that was measured with the brightness of the background 30 [cd/m$^2$] and the brightness of the target $A_{11}$ . . . 30 [cd/m$^2$]. From this figure, it is clear such a phenomenon that the vision partially drops near GY and BP is common among the examinees although the color vision goes up and down to some extent according to a person. According to the embodiment, it is known that it was possible to correctly measure the color vision that receives the influences of the color taste or the saturation.

Embodiment 2

Figure 7:
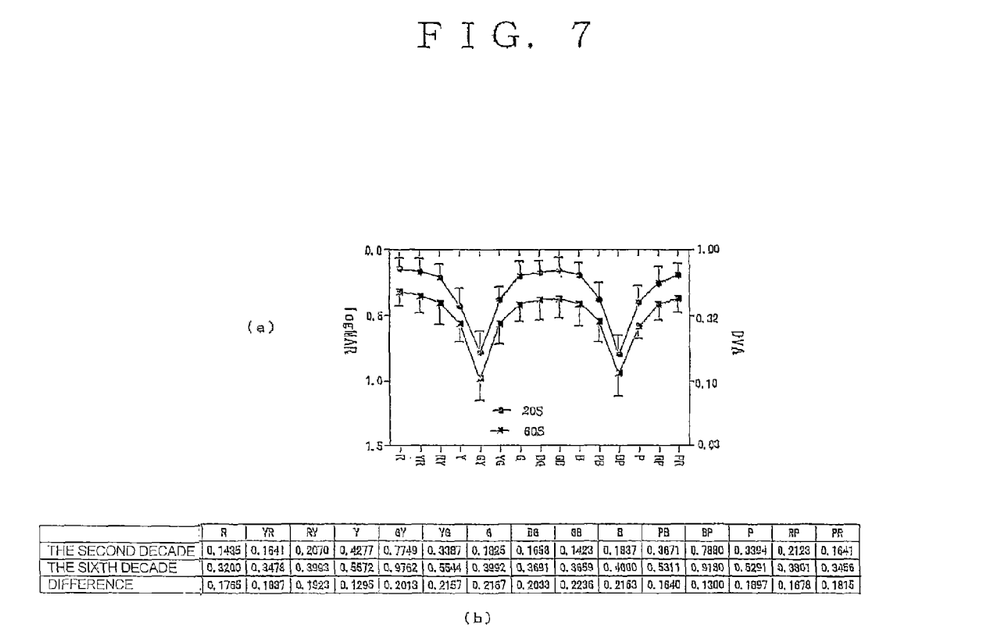

An embodiment 2 of the invention is now explained, referring to the appended FIGS. 7 (a) and (b).

FIG. 7 (a) is a view for comparison between the color vision in the sixth decade (the color vision of each color is a mean of seventeen males and five females) and the color vision in the second decade (the color vision of each color is a mean of five males and fourteen females), and FIG. 7(b) is a list that represents the measurement mean of the second decade, the measurement mean of the sixth decade and the different of both every each color. From FIG. 7(a), it is understood that the color vision of the examinees in the sixth decade is inferior to the color vision of the examinees in the second decade. Besides, from FIG. 7(b), it is understood that a degree of the deterioration of the vision by the aging varies according to a color, and the degree of the deterioration of R vision is for example 0.1765 that is higher than the Y vision, 0.1295.

EXPLANATION OF REFERENCE NUMBERS

1 . . . color-viewing function measuring means (vision test chart)
10 . . . color-viewing function measuring means
11 . . . display
12 . . . background indicator
13 . . . target indicator
14 . . . indication time controller
15 . . . perception detector
16 . . . color-viewing function judger
17 . . . target indication time memory
$A_{11}$, . . . targets (Landolt rings)
B . . . background

The invention claimed is:

1. Color-viewing function measuring means that indicates a plurality of targets that are colored in chromatic colors on a background and color vision and/or a color-viewing field that is a color-viewing function of an examinee is measured by testing whether the examinee can perceive each target, comprising:
    a display that is comprised of at least one of a liquid crystal display, a plasma display, an organic EL display and a CRT,
    a background indicator that indicates the background on the display,
    a target indicator that indicates the targets having a predetermined brightness, a predetermined color and a predetermined size on the display,
    an indication time controller that restricts time to indicate the target through the target indicator,
    a perception detector that outputs signal indicating that the examinee perceived the indicated target,
    and a color-viewing function judger that judges the color vision and/or the color-viewing field based upon the signals from the perception detector,
    wherein the background is an achromatic color, all of the plurality of targets or at least a predetermined number of the plurality of targets being colored in almost the same chromatic color; and the brightness of the targets being almost equal to the brightness of the background; whereby color vision and/or a color-viewing field regarding the chromatic color is measured.

2. The color-viewing function measuring means according to claim 1, wherein the brightness of all of the plurality of targets or the brightness of the predetermined number of targets are set almost equal to each other, and the following formula holds if the brightness of the target is α[cd/m2] and the brightness of the background is β[cd/m2]

$$-10 \leq \alpha - \beta \leq +10$$ [Formaula1].

3. The color-viewing function measuring means according to claim 2, wherein all of the plurality of targets or the predetermined number of targets are set to be almost equal to each other in their sizes, and the color-viewing field regarding the chromatic color of the examinee is measured by testing whether the examinee can perceive respective targets presented at various positions.

4. The color-viewing function measuring means according to claim 1, wherein all of the plurality of targets or the predetermined number of targets are set to be different in their sizes, and the color vision regarding the chromatic color of the examinee is measured by testing whether the examinee can perceive each target.

5. The color-viewing function measuring means according to claims 4, wherein all of the plurality of targets or the predetermined number of targets are set to be almost equal to each other in their sizes, and the color-viewing field regarding the chromatic color of the examinee is measured by testing whether the examinee can perceive respective targets presented at various positions.

6. The color-viewing function measuring means according to claim 1, wherein a target indication time memory stores target indication time for each color, and wherein an indication time controller that restricts the time to indicate the target through the target indicator to the target indication time for each color that is stored in the target indication time memory.

7. A color-viewing function measurement system, comprising:
   result input means that inputs measurement results regarding a color-viewing function that was measured through the color-viewing function measuring means according to claim 1;
   wherein the result input means inputs measurement results regarding the vision or the field of view that does not receive the influence of color taste, that is measured with the targets in almost achromatic color, or with the targets which are different from the background in brightness more than a predetermined brightness phases; and
   result comparison means that compares the measurement results regarding the color-viewing function and the measurement results regarding normal vision function with each other or indicates both.

8. The color-viewing function measurement system according to claim 7, comprising:
   result input means that inputs measurement results regarding the color-viewing function that was measured through the color-viewing function measuring means and
   result indication means that indicates a chromaticity diagram in the x-y axis plane, and the measurement results inputted through the result input means in the z axis plane.

9. The color-viewing function measurement system, comprising:
   result input means that inputs measurement results regarding the color-viewing function that was measured through the color-viewing function measuring means according claim 1;
   age input means that inputs age of the examinee that was measured through the color-viewing function measuring means;
   reference data storage that stores reference data regarding the color-viewing function previously for each age;
   a reference data extraction that extracts the reference data corresponding to age data from the reference data storage based upon the age data inputted through the age input means; and
   data comparison means that compares the measurement results inputted through the result input means and the reference data extracted through the reference data extraction with each other.

\* \* \* \* \*